(12) United States Patent
Gardlik et al.

(10) Patent No.: US 9,216,945 B2
(45) Date of Patent: *Dec. 22, 2015

(54) METHODS OF SYNTHESIZING 2-SUBSTITUTED-1,4-BENZENEDIAMINE

(71) Applicant: The Procter & Gamble Company, Cincinnati, OH (US)

(72) Inventors: John Michael Gardlik, Cincinnati, OH (US); Garry Steven Garrett, Fairfield, OH (US); Bryan Patrick Murphy, Loveland, OH (US); Guiru Zhang, Lebanon, OH (US); Robert Edward Shumate, Hamilton, OH (US); James S. Anderson, Bethel, CT (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/085,617

(22) Filed: Nov. 20, 2013

(65) Prior Publication Data

US 2014/0081049 A1    Mar. 20, 2014

Related U.S. Application Data

(62) Division of application No. 13/016,322, filed on Jan. 28, 2011, now Pat. No. 8,618,326.

(60) Provisional application No. 61/387,727, filed on Sep. 29, 2010, provisional application No. 61/419,530, filed on Dec. 3, 2010.

(51) Int. Cl.

| C07C 215/00 | (2006.01) |
| C07C 209/00 | (2006.01) |
| C07C 213/00 | (2006.01) |
| C07C 217/00 | (2006.01) |
| C07C 211/00 | (2006.01) |
| C07C 217/84 | (2006.01) |
| C07C 209/10 | (2006.01) |
| C07C 209/32 | (2006.01) |

(52) U.S. Cl.
CPC ............. *C07C 217/84* (2013.01); *C07C 209/10* (2013.01); *C07C 209/32* (2013.01)

(58) Field of Classification Search
None
See application file for complete search history.

(56) References Cited

U.S. PATENT DOCUMENTS

| 2,273,564 A | 2/1942 | Dickey |
| 4,997,451 A | 3/1991 | Clausen |
| 6,648,923 B1 | 11/2003 | Goettel |
| 7,445,645 B2 | 11/2008 | Sabelle |

FOREIGN PATENT DOCUMENTS

| DE | 3731202 A1 | 7/1989 |
| EP | 1765267 B1 | 5/2005 |
| JP | S57134449 | 8/1982 |
| JP | H0537420 | 5/1993 |
| JP | H1112239 | 1/1999 |

OTHER PUBLICATIONS

Kudo; Synthesis and Herbicidal Activity of 1,5-Diarylpyrazole Derivatives; Jun. 1999; Chem. Pharm. Bull. 47(6) 857-868; 12 pages.
Mehenni; *Synthesis and Characterization of Novel Conducting Homopolymers Bases on Amino β-styryl Terthiophene*; Canadian Journal of Chemistry 86 (11), 1010-1018, 2008.
*Finkelstein Reaction*; Wikipedia summary, 2 pages, 1910.
Dorretijn; *The Reactivity of o-Hydroxybenzyl Alcohol and Derivatives in Solution at Elevated Temperatures*; J. Org. Che.m. 1999, 64, 3012-3018.
Rondestvedt; *Meth-Terminated Perfluoroalkyl Iodides and Related Compounds*; J. Org. Chem., vol. 42, No. 11, 1977, 1985-1990.
Silk; *The Snythesis of 3-Chloro-4-nitro- and 4-Amino-3-chlorobenzyl Alcohols*; 7 pgs, 1987.

*Primary Examiner* — Clinton Brooks
(74) *Attorney, Agent, or Firm* — James T. Fondriest

(57) ABSTRACT

Disclosed is a method of making a 2-substituted-1,4-benzenediamine by nucleophilic aromatic substitution.

7 Claims, 6 Drawing Sheets

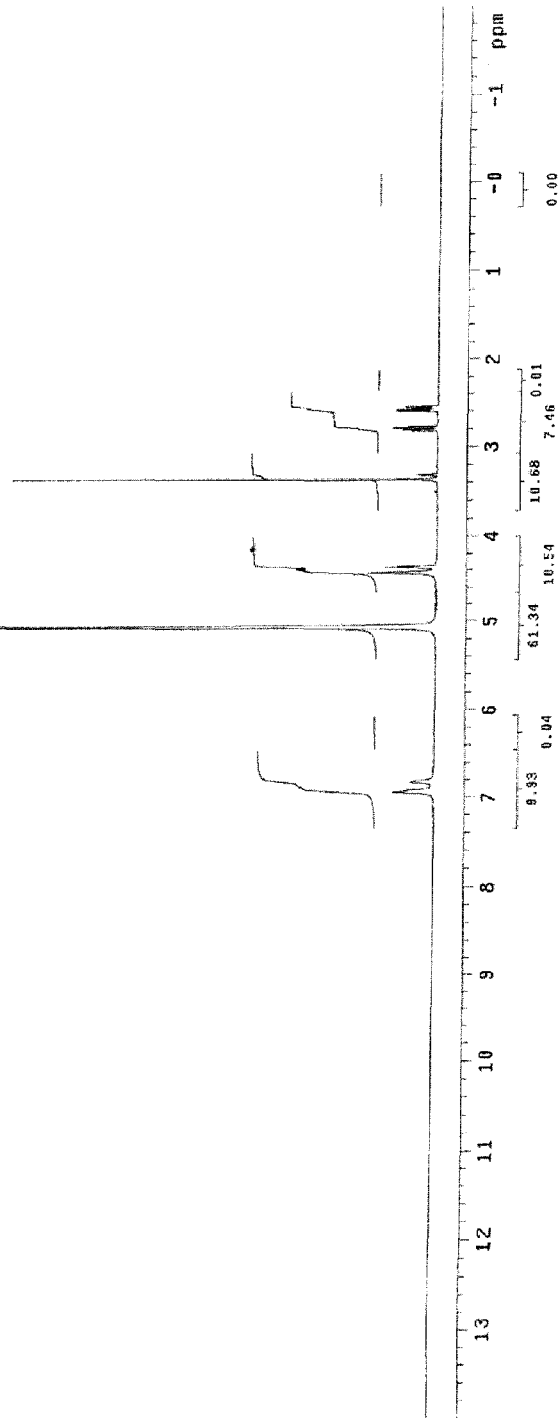

METHODS OF SYNTHESIZING 2-SUBSTITUTED-1,4-BENZENEDIAMINE

FIELD OF THE INVENTION

The subject matter of the present application relates to the synthesis of a 2-substituted-1,4-benzenediamine such as a 2-methoxymethyl-1,4-benzenediamine and physiologically compatible salts thereof.

BACKGROUND OF THE INVENTION

2-Substituted-1,4-benzenediamine and physiologically compatible salts thereof may be useful as primary intermediates in oxidative hair color. For example, 2-methoxymethyl-1,4-benzenediamine and physiologically compatible salts thereof are useful as primary intermediates in oxidative hair color. A current process for synthesizing 2-methoxymethyl-1,4-benzenediamine may be accomplished as discussed in U.S. Pat. Nos. 4,997,451 and 6,648,923. Such a process is illustrated by the following reaction scheme:

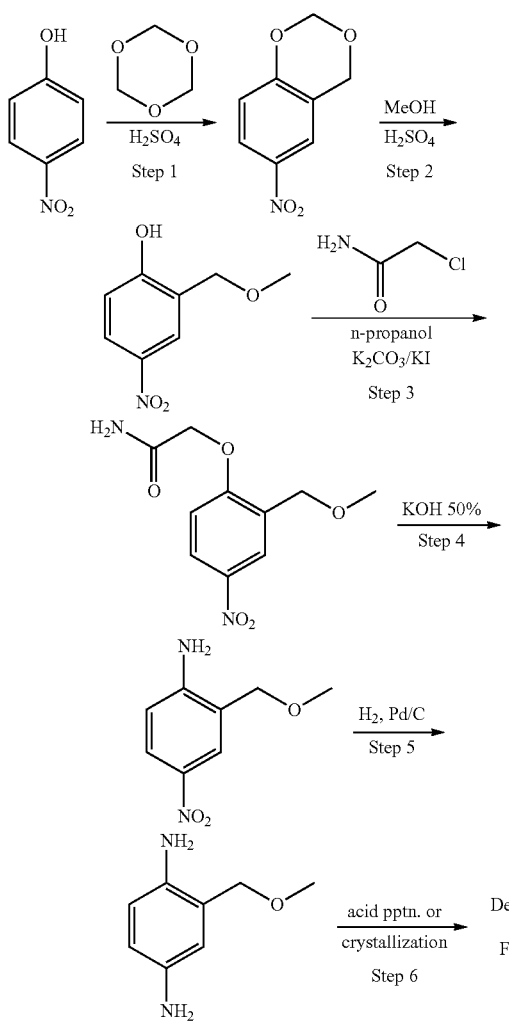

However, it is still desired to find alternative processes that reduce costs of manufacturing the desired product. As such, there still exists a need to utilize less expensive starting materials to arrive at the desired product.

SUMMARY OF THE INVENTION

One embodiment of the present application relates to a method for making 2-substituted-1,4-benzenediamine comprising: (a) introducing ammonia to a 4-nitro-2- (or 3-) substituted-chlorobenzene to obtain a 4-nitro-2- (or 3-)substituted-aminobenzene:

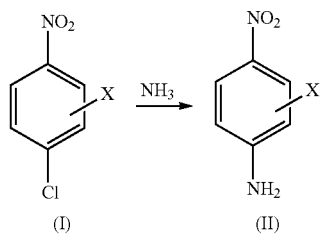

(b) hydrogenating the 4-nitro-2- (or 3-) substituted-aminobenzene in the presence of a hydrogenation catalyst to form a 2-substituted-1,4-benzenediamine:

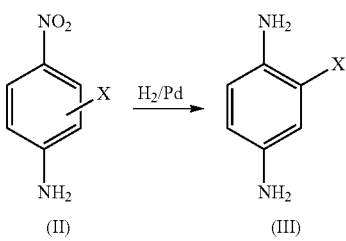

wherein X of formulae (I)-(III) is selected from the group consisting of: (a) an C1-C6 alkyl; (b) methoxy, ethoxy, propoxy, isopropoxy, butoxy; (c) C1-C6 alkyl with hydroxy substitution; (d)-(CH2)yOCH3; wherein y is from 1-3; (e) —(CH2)yOCH2CH3; wherein y is from 1-3; (f)-(CH2)yOCH2CH2CH3; wherein y is from 1-3; (g)

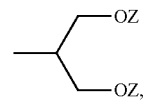

wherein Z is hydrogen or C1-3 alkyl; and (h) mixtures thereof.

Another embodiment of the present application relates to the method for making 2-substituted-1,4-benzenediamine comprising: (a) introducing ammonia to 4-nitro-2-substituted-chlorobenzene to obtain 4-nitro-2-substituted-aminobenzene:

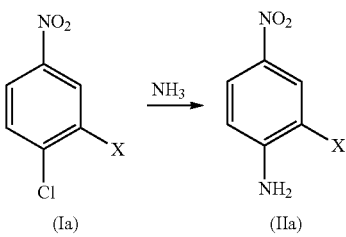

(b) hydrogenating the 4-nitro-2-substituted-aminobenzene in the presence of a hydrogenation catalyst to form a 2-substituted-1,4-benzenediamine

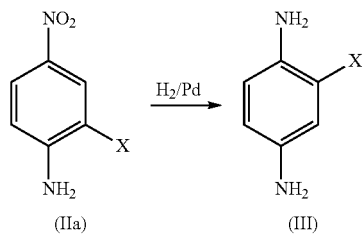

wherein X of formulae (Ia), (IIa) and (III) is selected from the group consisting of: (a) a C1-C6 alkyl; (b) methoxy, ethoxy, propoxy, isopropoxy, butoxy; (c) a C1-C6 alkyl with hydroxy substitution; (d) —(CH2)yOCH3; wherein y is from 1-3; (e) —(CH2)yOCH2CH3; wherein y is from 1-3; (f) —(CH2)yOCH2CH2CH3; y is from 1-3; (g)

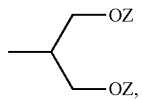

wherein Z is hydrogen or C1-3 alkyl; and (h) mixtures thereof.

Another embodiment of the present application relates to a method for making 2-substituted-1,4-benzenediamine comprising: (a) introducing ammonia to 4-nitro-3-substituted-chlorobenzene to obtain 4-nitro-3-substituted-aminobenzene:

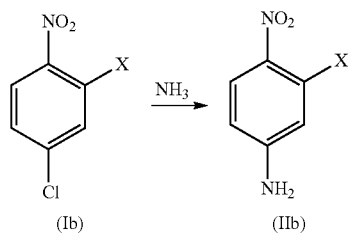

(b) hydrogenating the 4-nitro-3-substituted-aminobenzene in the presence of a hydrogenation catalyst to form a 2-substituted-1,4-benzenediamine:

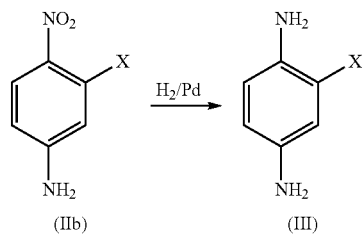

wherein X of formulae (Ib), (IIb) and (III) is selected from the group consisting of: (a) a C1-C6 alkyl; (b) methoxy, ethoxy, propoxy, isopropoxy, butoxy; (c) a C1-C6 alkyl with hydroxy substitution; (d) —(CH2)yOCH3; wherein y is from 1-3; (e) —(CH2)yOCH2CH3; wherein y is from 1-3; (f) —(CH2)yOCH2CH2CH3; wherein y is from 1-3; (g)

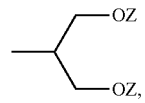

wherein Z is hydrogen or C1-3 alkyl; and (h) mixtures thereof.

Another embodiment of the present application relates to a method of making 2-methoxymethyl-1,4-benzenediamine comprising the steps: (a) introducing ammonia to a 4-nitro-3-methoxymethyl-chlorobenzene to obtain 4-nitro-3-methoxymethyl-aminobenzene; and (b) hydrogenating the 4-nitro-3-methoxymethyl-aminobenzene in the presence of a hydrogenation catalyst to obtain the 2-methoxymethyl-1,4-benzenediamine.

Another embodiment of the present application relates to a method of making 2-methoxymethyl-1,4-benzenediamine comprising the steps: (a) nitrating 3-halobenzylhalide to obtain 4-nitro-3-halomethylhalobenzene; (b) converting the 3-halomethyl group to a 3-methoxymethyl group to obtain 4-nitro-3-methoxymethyl-halobenzene; (c) introducing ammonia to the 4-nitro-3-methoxymethyl-halobenzene to obtain 4-nitro-3-methoxymethyl-aminobenzene; and (d) hydrogenating the 4-nitro-3-methoxymethyl-aminobenzene in the presence of a hydrogenation catalyst to obtain the 2-methoxymethyl-1,4-benzenediamine.

BRIEF DESCRIPTION OF THE DRAWINGS

FIG. 6 shows an $^1$H NMR scan for 2-methoxymethyl-1,4-benzenediamine as an Adduct with malic acid of the described method and process.

DETAILED DESCRIPTION OF THE INVENTION

Figure 1:
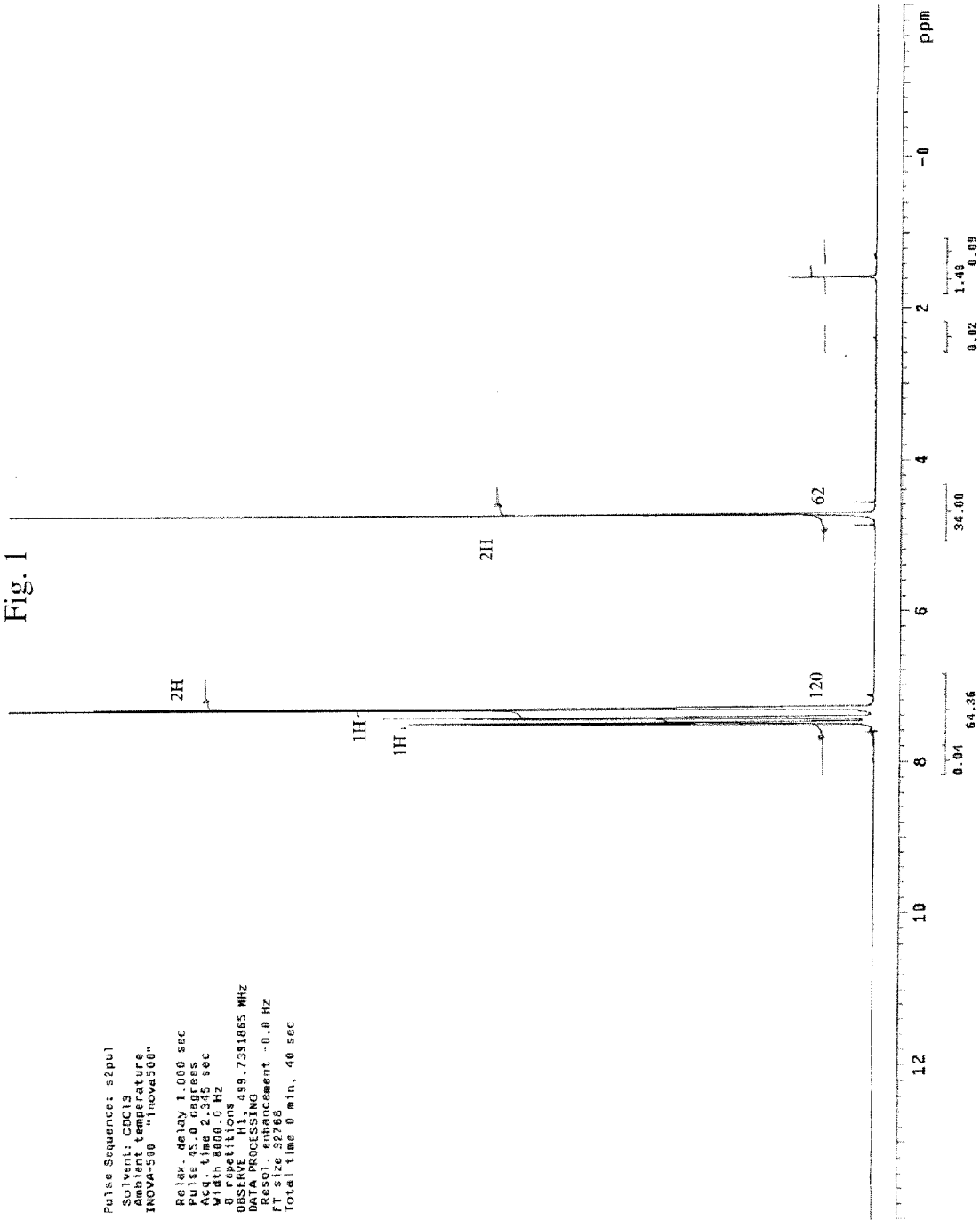
FIG. 1 shows an $^1$H NMR scan of formula (XVI) of the described method and process.

It has now been found that the a 2-substituted-1,4-benzenediamine can be produced effectively from the following described process. One preferred compound 2-methoxymethyl-1,4-benzenediamine shown in formula (IV):

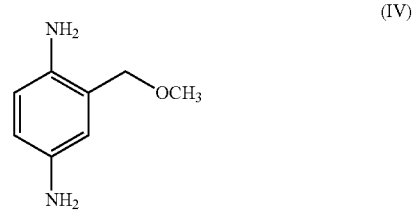 [SMILES: COCc1cc(N)ccc1N]

is obtainable in a simple manner without a need for further purification steps.

Accordingly, a method of making the 2-substituted-1,4-benzenediamine includes an ammonia step followed by a hydrogenation step.

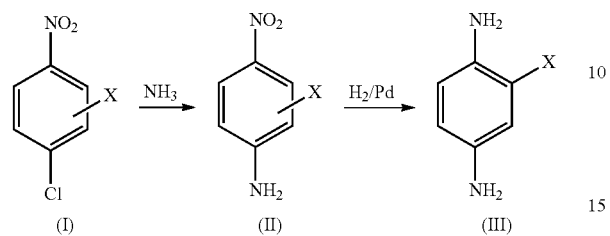

Wherein X of formulae (I)-(III) is selected from the group consisting of:
- (a) a C1-C6 alkyl, such as methyl, ethyl, propyl, butyl;
- (b) methoxy, ethoxy, propoxy, isopropoxy, butoxy;
- (c) C1-C6 alkyl with hydroxy substitution;
- (d) —(CH2)yOCH3; y is from 1-3;
- (e) —(CH2)yOCH2CH3; y is from 1-3;
- (f) —(CH2)yOCH2CH2CH3; y is from 1-3;
- (g)

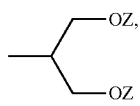

Z is hydrogen or C1-3 alkyl;
and mixtures thereof.

As used herein "physiologically compatible salts" means salts that are suitable to be used with humans and have limited to no irritancy to humans.

The substitution of the X moiety can be on the 2 or the 3 position of the benzene ring as shown below.

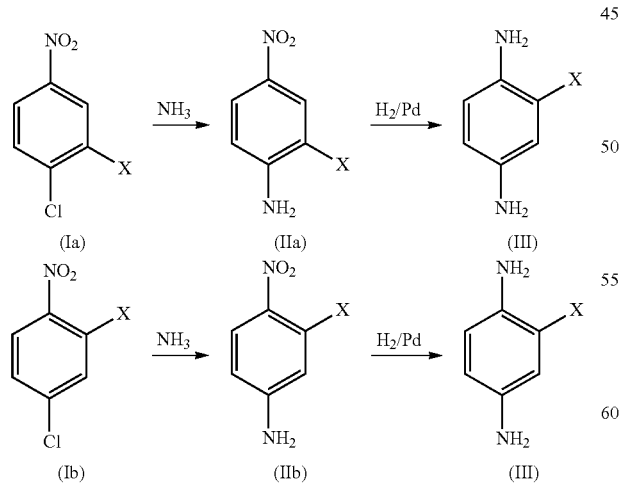

Accordingly, the method described may be utilized for making 2-methoxymethyl-1,4-benzenediamine shown in formula (IV) via either isomer shown below.

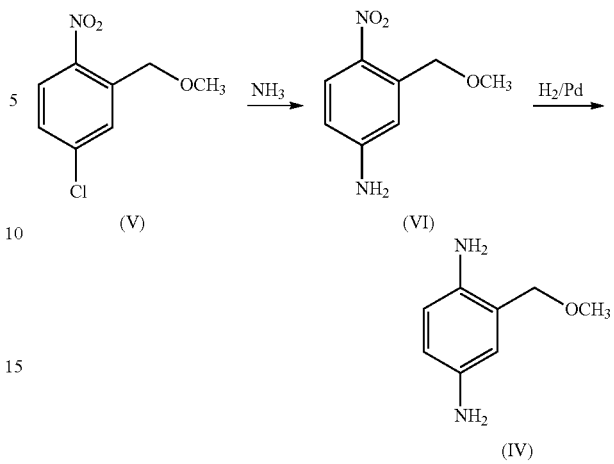

3-substitution isomer to form 2-methoxymethyl-1,4-benzenediamine

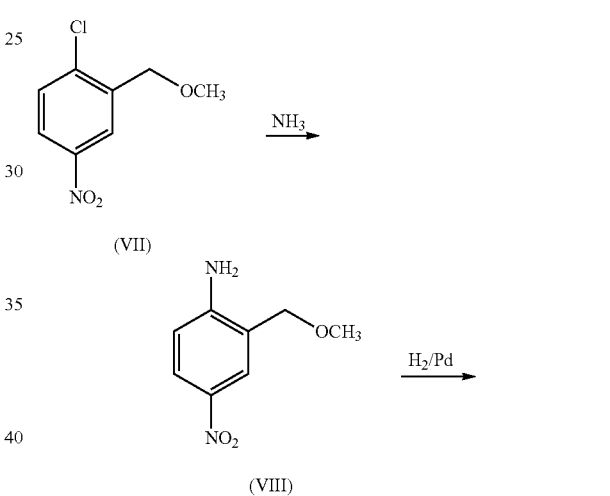

2-substitution isomer to form 2-methoxymethyl-1,4-benzenediamine

The Ammonia Step

The Ammonia Step of the reaction scheme above comprises introducing ammonia (e.g., anhydrous ammonia) to a 4-nitro-2 (or 3-) substituted-chlorobenzene shown in formula (I) to obtain the 4-nitro-2 (or 3-) substituted-aminobenzene intermediate product shown in formula (II) through nucleophilic displacement. In one embodiment the 4-nitro-2- (or 3-) substituted-aminobenzene intermediate product is a 4-nitro-2- (or 3-) methoxymethyl-aminobenzene (the aminobenzene may also be known as a aniline). Normally, only aromatic fluoro atoms can be displaced, but with the specific substitution pattern detailed herein, the chloro atom also has sufficient activity to be displaced. Alternatively, the chloro atom can be exchanged for a fluoro atom, (for example, but not limited to, by using potassium fluoride and 18-crown-6), either in situ during the reaction with ammonia, or in a discrete step prior to treatment with ammonia. See Finkelstein, H. *Ber.*, 1910, 43, 1528.

Embodiments of the ammonia step may include mixing liquid ammonia with the 4-nitro-2 (or 3-)substituted-chlorobenzene in a stirred reactor, charging the reactor with nitrogen to a pressure which is within a range of between about 75 psig (89.7 psi or 618 kPa) and about 100 psig (114.7 psi or 791 kPa), heating the mixture to a temperature within a range of about 150° C. to about 220° C., more typically about 180° C. to about 200° C., and stirring the mixture at this temperature for a time period of about 1 hour to about 20 hours. Embodiments of the ammonia step may be carried out in a solvent. Examples of such solvents include, but are not limited to, formamide or acetonitrile.

The Hydrogenation Step

The Hydrogenation Step of the reaction scheme above comprises hydrogenating the 4-nitro-2- (or 3-)substituted-aminobenzene intermediate product shown in formula (II) in the presence of a hydrogenation catalyst (e.g., a palladium, platinum, or nickel based catalyst such as Raney Nickel) to obtain the 2-substituted-1,4-benzenediamine shown in formula (III). The catalytic hydrogenation reaction may occur in a hydrogenation solvent such as ethyl acetate, toluene, butyl acetate, ethanol, methanol, and mixtures thereof.

Embodiments of the hydrogenation step may include mixing the 4-nitro-2 (or 3) substituted-aminobenzene with a hydrogenation catalyst and a solvent, applying a hydrogen atmosphere of about 50-60 psig (64.7-74.7 psi or 446-515 kPa) pressure over the reaction mixture, and stirring the mixture under hydrogen atmosphere for a period of about 30 minutes to about 4 hours. Alternatively, the reaction mixture may be heated under an atmosphere of hydrogen to a temperature within a range of about 20° C. to about 80° C., more typically about 60° C. to about 80° C. In addition, embodiments of the hydrogenation step may further include the sub-steps of filtering, washing and drying the 2-substituted-1,4-benzenediamine.

Optional Etherification Step

An optional step in the present process comes before the ammonia step and a 4-nitro-2 (or 3-)halomethyl substituted chlorobenzene is introduced to an alcohol or alkoxide, which are the ether forming agents, which results in an ether derivative of the 4-nitro-2- (or 3-)substituted chlorobenzene.

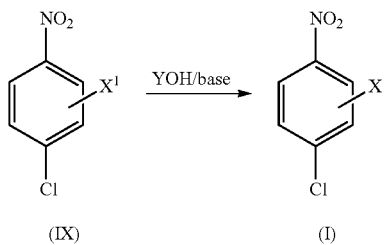

Wherein $X^1$ of formula (IX) is selected from a halogen, such as F, Cl and Br; a C1-C4 haloalkyl such as a fluoromethyl, chloromethyl, bromomethyl bromide, fluoroethyl, chloroethyl, bromoethyl and the like;

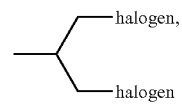

wherein the halogen is F, Cl or Br, and mixtures thereof.

Y of YOH represents an alkyl moiety of C1-C4, such as methyl, ethyl, propyl and butyl. The base may be selected from an alkali alkoxide and/or alkali hydroxide Wherein X of formula (I) is selected from the group consisting of: (b) methoxy, ethoxy, propoxy, isopropoxy, butoxy (d) —(CH2)yOCH3; y is from 1-3 (e) —(CH2)yOCH2CH3; y is from 1-3 (f) —(CH2)yOCH2CH2CH3; y is from 1-3 (g)

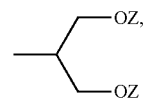

Z is hydrogen or C1-3 alkyl; and mixtures thereof.
The substitution of the $X^1$ and X moiety can be on the 2 or the 3 position of the benzene ring as shown below.

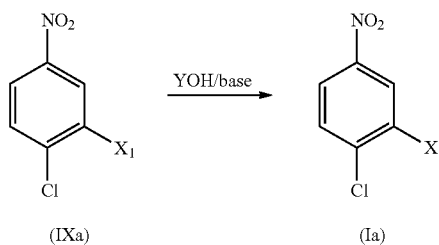

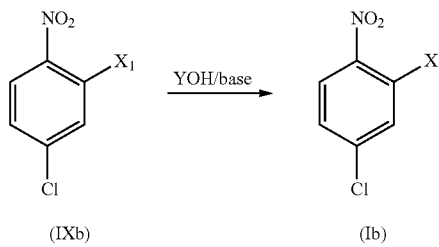

Wherein $X^1$, X and Y of YOH are as defined above formula (IX) and (I).

Accordingly, the method described may be utilized for making the 2-methoxymethyl-1,4-benzenediamine shown in formula (IV) via an isomer shown below (via a 2-positional isomer).

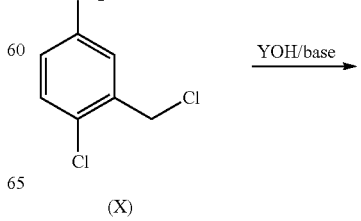

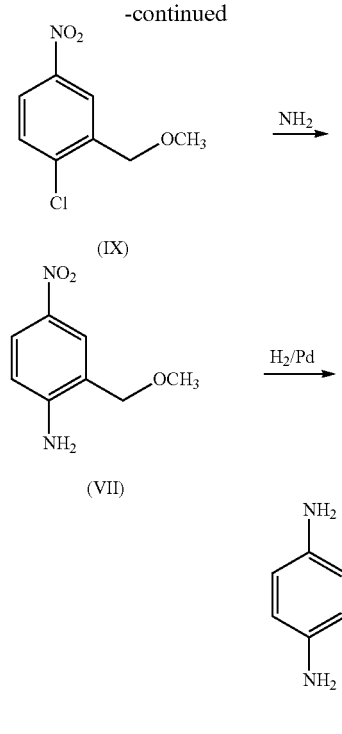

(IX)

(VII)

(IV)

wherein Y of YOH is methyl for methanol.

The 3-positional isomers of IX, X, and VII are also suitable to form the 2-methoxymethyl-1,4-benzenediamine.

The Optional Etherification Step of the reaction scheme comprises introducing a ether forming group to the 4-nitro-2 (or 3-)haloalkyl moiety substituted-chlorobenzene intermediate product shown in formula (IX) to obtain the 4-nitro-2 (or 3-) substituted-chlorobenzene intermediate product shown in formula (I) through nucleophilic displacement.

A solution of base such as an alkali alkoxide and/or alkali hydroxide in a C1-C3 alcohol (methanol, ethanol, and propanol) may provide the ether forming group.

Non-limiting examples of suitable alkali alkoxide include sodium methoxide, lithium methoxide, potassium methoxide, sodium ethoxide, lithium ethoxide, potassium ethoxide, sodium propoxide, lithium propoxide, potassium propoxide, and mixtures thereof. Non-limiting examples of suitable alkali hydroxides include sodium hydroxide and potassium hydroxide. The concentration of alkali alkoxide and/or alkali hydroxide in a C1-C3 alcohol ranges from about 10% to about 30%, more typically about 20%.

Embodiments of the etherification step may include mixing the 4-nitro-2 (or 3-) haloalkylhalobenzene with the ether forming agent (e.g., alkali alkoxide and/or alkali hydroxide solution), stirring at room temperature or optionally heating under reflux in a C1-C4 alcohol, such as methanol, and stirring the mixture at this temperature for a period of about 30 minutes to about 2 hours. Other embodiments of the etherification step further include an additional sub-step of first dissolving the 4-nitro-2 (or 3-) haloalkyl moiety substituted-chlorobenzene in methanol, ethanol, propanol, or butanol before mixing with the alkali alkoxide and/or alkali hydroxide solution.

Optional Etherification with Alkyl Halides

Alternatively, the etherification step may utilize a solution of a base such as an alkali alkoxide and/or alkali hydroxide and an alkyl halide may provide the ether forming group.

Another optional step in the present process takes place before the ammonia step wherein a 4-nitro-2 (or 3-)substituted-chlorobenzene is introduced to an alkyl halide which results in an ether derivative of the 4-nitro-2- (or 3-)substituted chlorobenzene.

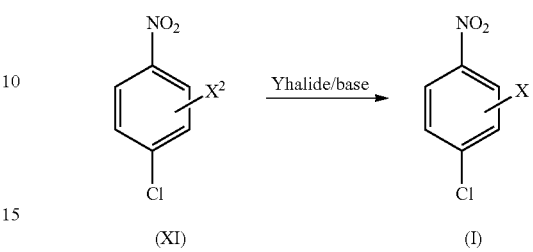

Wherein $X^2$ of formula (XI) is selected from the group consisting of, —(CH2)yOH; y is from 1-3;

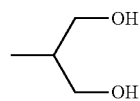

and mixtures thereof.

Y of the Yhalide, representing the alkyl halide ether forming agent, can be a C1-C4 alkyl. The "halide" of the Yhalide may be a halogen, such as F, Cl or Br.

The base is an alkali alkoxide and/or alkali hydroxide.

Wherein X of formula (I) is selected from the group consisting of: (d) —(CH2)yOCH3; y is from 1-3 (e) —(CH2)yOCH2CH3; y is from 1-3 (f) —(CH2)yOCH2CH2CH3; y is from 1-3 (g)

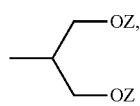

Z is C1-C4 alkyl; and mixtures thereof.

The $X^2$ or X moiety substitution may be on the 2- or the 3-position of the benzene ring.

Optional Bromination/Methoxylation Step

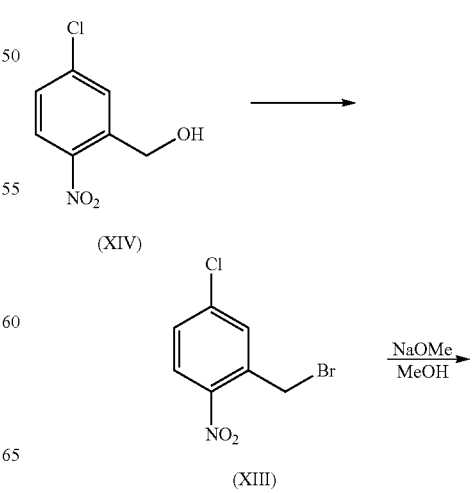

(XIV)

(XIII)

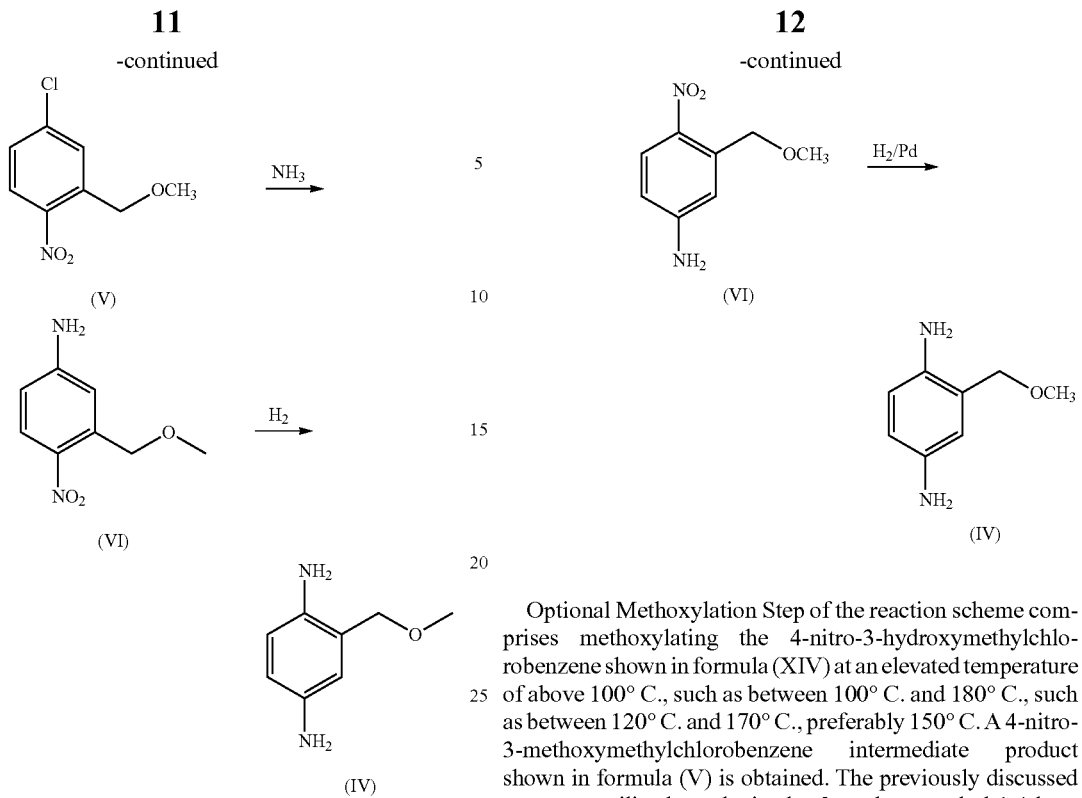

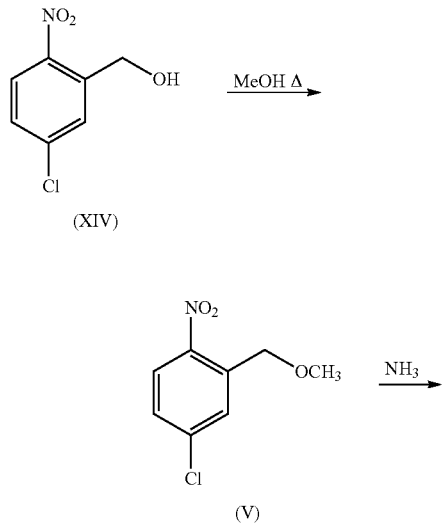

Optional Bromination/Methoxylation Step of the reaction scheme comprises brominating the 4-nitro-3-hydroxymethylchlorobenzene shown in formula (XII) with bromine gas (Br2) and triphenylphosphine to obtain formula (XIII) followed by reacting with methanol to obtain the 4-nitro-3-methoxymethylchlorobenzene intermediate product shown in formula (IX). The previously discussed steps are utilized to obtain the 2-methoxymethyl-1,4-benzenediamine shown in formula (IV).

Optional Methoxylation Step of the reaction scheme comprises methoxylating the 4-nitro-3-hydroxymethylchlorobenzene shown in formula (XIV) at an elevated temperature of above 100° C., such as between 100° C. and 180° C., such as between 120° C. and 170° C., preferably 150° C. A 4-nitro-3-methoxymethylchlorobenzene intermediate product shown in formula (V) is obtained. The previously discussed steps are utilized to obtain the 2-methoxymethyl-1,4-benzenediamine shown in formula (IV). (See J. Org. Chem. 1999, 64, 3012-3018). This optional methoxylation step may also be performed via the Williamson ether synthesis or any number of ways common to those skilled in the art.

Optional Nitrating Step

An optional step in the present process comes before the etherification step that is a nitrating step of a chlorobenzene.

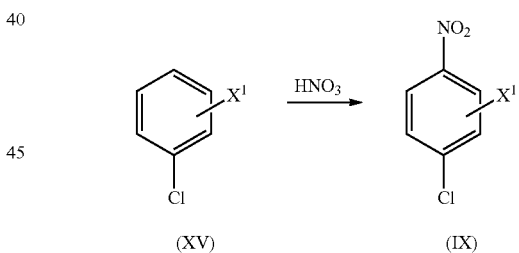

Wherein $X^1$ of formulae (XV) and (IX) is selected from a C1-C4 alkyl halogen such as a methyl fluoride, methyl chloride, methyl bromide, ethyl fluoride, ethyl chloride, ethyl bromide and the like;

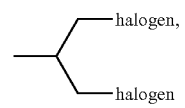

and mixtures thereof, such as F, Cl, Br and mixtures thereof; a C1-C6 alkyl; C1-C6 alkyl or with hydroxy substitution; —(CH2)yOCH3; wherein y is from 1-3; —(CH2)yOCH2CH3; wherein y is from 1-3; —(CH2)yOCH2CH2CH3; wherein y is from 1-3;

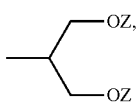

wherein Z is hydrogen or C1-C3 alkyl; and mixtures thereof.

Accordingly, the method described may be utilized for making the 2-methoxymethyl-1,4-benzenediamine shown in formula (IV) via the 2-position isomer shown below.

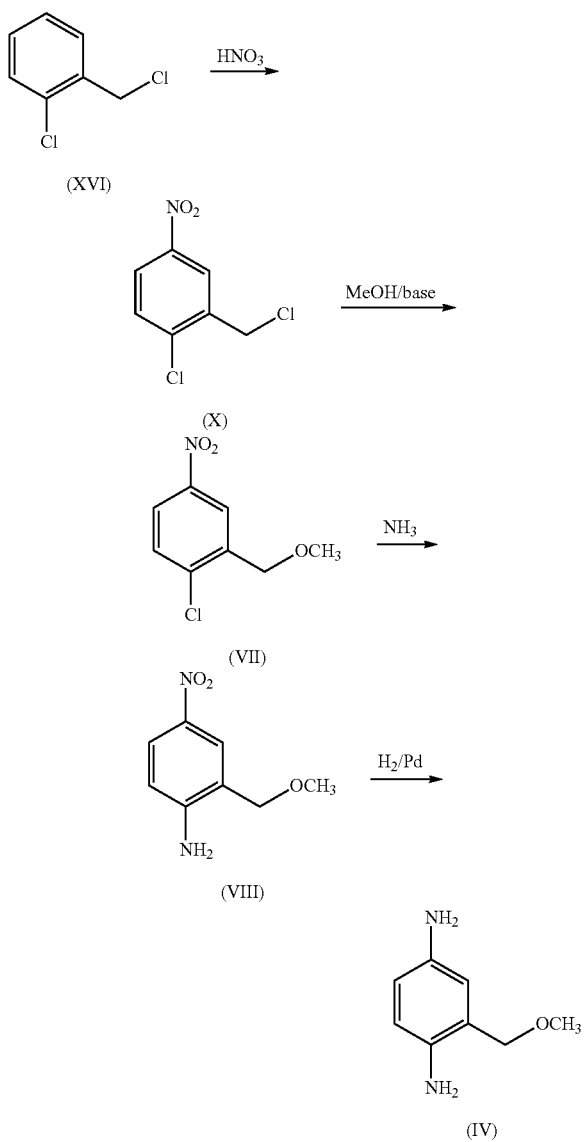

Optional Nitrating Step of the reaction scheme comprises nitrating the 2-chlorobenzylchloride shown in formula (XVI) to obtain the 4-nitro-2-chloromethylchlorobenzene intermediate product shown in formula (X). Such a nitrating step is described in the Journal of Chemical Research Synopses (8), 247, 1987, and the Canadian Journal of Chemistry 86 (11), 1010-1018, 2008.

Optional Acid Precipitating Step

Optional Acid Precipitating Step of the reaction scheme comprises acid precipitating the 2-substituted-1,4-benzenediamine shown in formula (III) to obtain a specifically desired salt. Embodiments of the Acid Precipitating Step may include adding the 2-substituted-1,4-benzenediamine, such as 2-methoxymethyl-1,4-benzenediamine, to an acid solution that contains a reductant (e.g., sodium sulfite) to prevent oxidation, while utilizing external cooling to maintain the reaction at a temperature within a range of about 0° C. to about 40° C., more typically about 10° C. to about 30° C., over a period of about 30 minutes to 3 hours until the salt crystallizes out of the solution. However, the reverse addition of adding the acid solution to a solution of the 2-substituted-1,4-benzenediamine containing a reductant, such as 2-methoxymethyl-1,4-benzenediamine, is also suitable. Non-limiting examples of suitable acid solutions include malic acid, sulfuric acid, hydrochloric acid, phosphoric acid and tartaric acid. In addition, embodiments of the Acid Precipitating Step may further include the sub-steps of filtering, washing and drying the salt of the 2-substituted-1,4-benzenediamine, such as 2-methoxymethyl-1,4-benzenediamine salt.

The following examples illustrate the above-described syntheses, but do not limit the broad concept of the invention.

EXAMPLE 1

Preparation of 2-methoxymethyl-1,4-benzenediamine

The Nitrating Step—Preparation of 4-nitro-2-chloromethylchlorobenzene.

Figure 2:
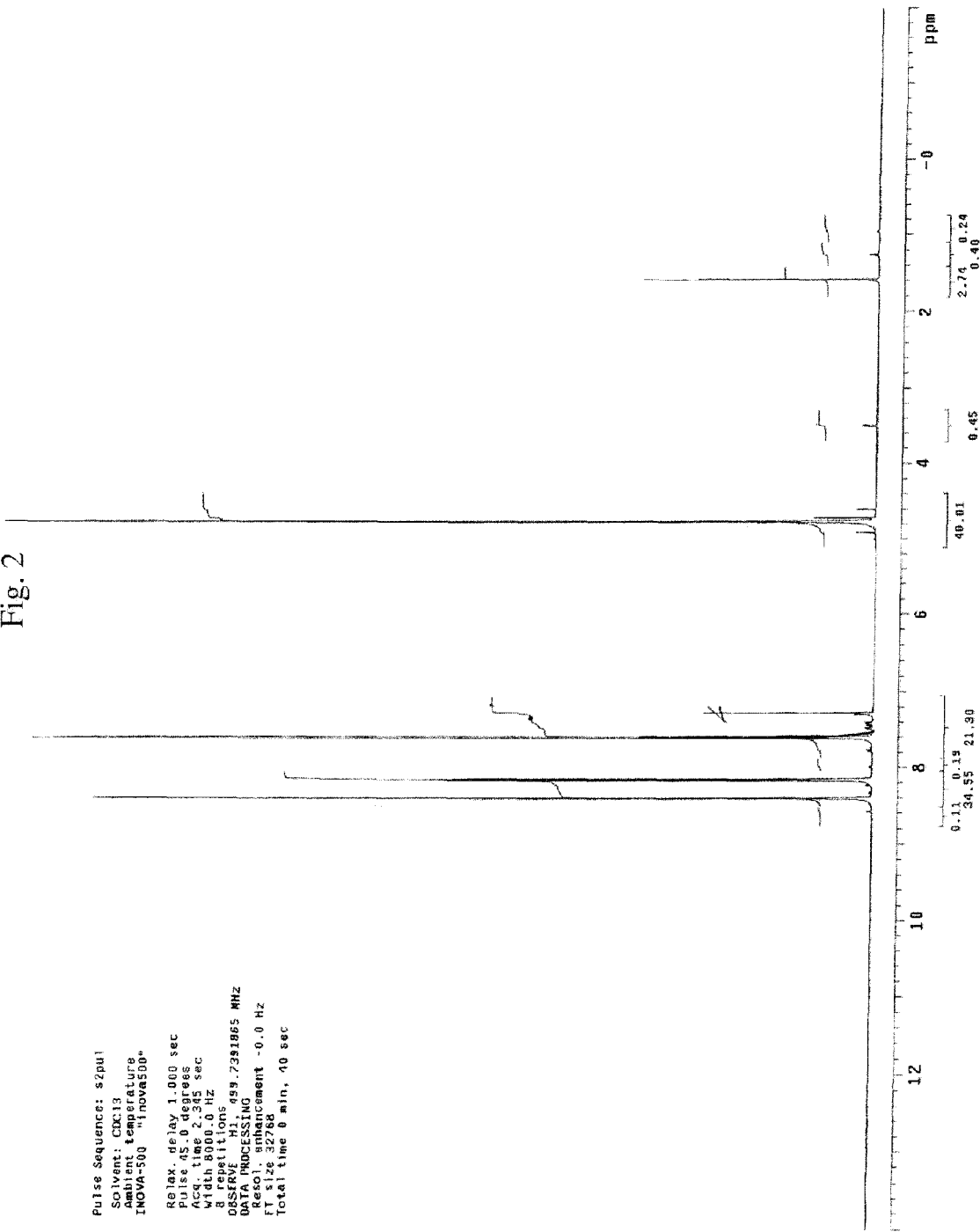
FIG. 2 shows an $^1$H NMR scan of formula (X) of the described method and process.

50.0 g (0.31 mol) of 2-chlorobenzyl chloride (see FIG. 1) is dissolved in 141 ml of concentrated sulfuric acid and cooled in an ice/methanol bath to an internal temperature of −5° C. 20.66 g (0.328 mol) of fuming nitric acid is placed in an attached addition funnel. The nitric acid is added at such a rate as to keep the internal temperature below 0° C. Near the end of the reaction the product precipitates from the solution and stirring ceases. The reaction mixture is poured over 750 ml of ice in a 1 liter Erlenmeyer flask. Additional ice is added to keep reaction cold. The cold reaction is allowed to stand so that the solids settle. The supernate is poured off. The solid is triturated with 250 ml water. The final solid is dissolved in 400 ml dichloromethane and washed with two (2) 200 ml portions of saturated sodium bicarbonate solution. The dichloromethane phase is then dried (sodium sulfate), filtered and evaporated. The product, 4-nitro-3-chloromethylchlorobenzene (56 g, 0.272 mol) is obtained as a semi-solid and used without further purification. $^1$H-NMR (CDCl$_3$): 8.41 (d), 1H, 8.17 (dd) 1H, 7.594 (d), 1H, 4.756 (s), 2H. See FIG. 2.

The Methoxymethylation Step—Preparation of 4-Nitro-2-methoxymethylchlorobenzene.

Figure 3:
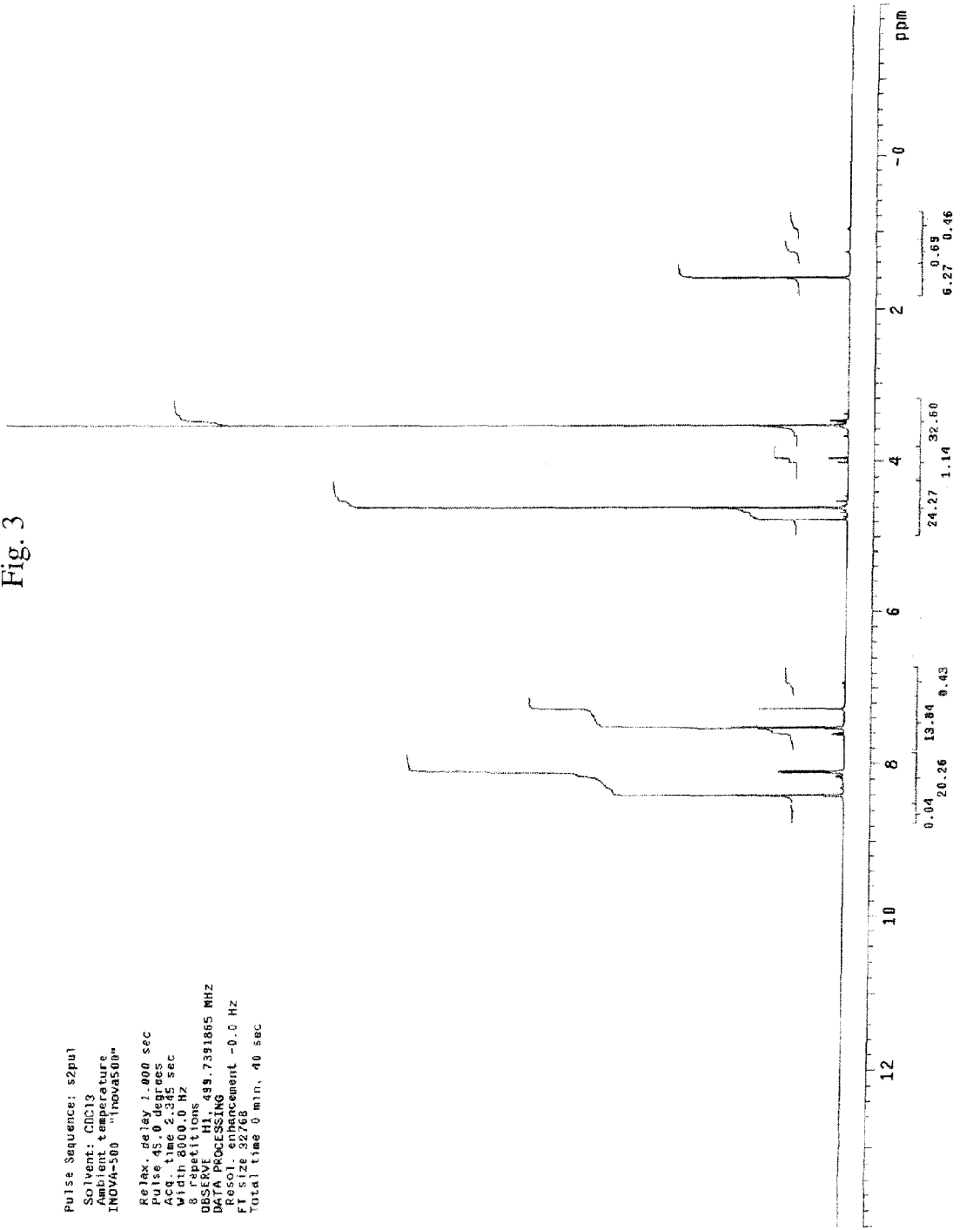
FIG. 3 shows an $^1$H NMR scan for formula (VII) of the described method and process.

Embodiment A: Utilizing an Alkali Methoxide 15.0 g (72.8 mmol) of 4-nitro-2-chloromethylchlorobenzene is stirred in 50 ml of anhydrous methanol. At room temperature, 13.9 g of a sodium methoxide solution (30% in methanol) is added. In the course of the addition, sodium chloride precipitates out and a colorless to rose-colored suspension is obtained. The addition of the sodium methoxide solution is finished after 30 minutes, during which time the internal temperature rises to approximately 30° C. Then the reaction mixture is heated for 30 minutes under reflux, and the suspension is filtered hot to obtain a clear solution. Upon cooling, the product, 4-nitro-2-methoxymethylchlorobenzene, crystallizes out and is filtered off. The product yield is 11.0 g of a yellowish solid. The filtrate is concentrated to approximately half of the volume and cooled in an ice bath to give another 3.8 g of product. The total product yield is 14.8 g. ¹H-NMR (DMSO-d₆): 8.27 (d), 1H, 8.18 (dd), 1H, 7.77 (d), 1H, 4.58 (s), 2H, 3.44 ppm (s), 3H. See FIG. 3.

Embodiment B: Utilizing an Alkali Hydroxide 180.0 g of 4-nitro-2-chloromethylchlorobenzene is stirred in 450 ml of anhydrous methanol. After heating to reflux, a prepared solution of 41.9 g of sodium hydroxide in 270 ml of methanol is added over a period of one hour. In order to complete the reaction the mixture is stirred under reflux for an additional hour. In the course of the addition, sodium chloride precipitates out and a yellowish suspension is obtained. After completion of the reaction, the suspension is cooled in an ice bath. Under continuous cooling at less than 10° C., a solution of 90 ml acetic acid in 540 ml water is added over of a period of 15 minutes. After addition, the suspension is stirred in an ice bath for an additional 30 minutes. Finally, the reaction product, 4-nitro-3-methoxymethylchlorobenzene, is filtered off and washed with a mixture of water and methanol (9:1). The product is dried at 40° C. The product yield is 165.4 g.

Preparation of
4-nitro-3-methoxymethylchlorobenzene 5.61 g of 5-chloro-2-nitrobenzyl alcohol is mixed with 9.1 g of triphenylphosphine in 100 ml of dichloromethane. To this solution 6.1 g of N-bromosuccinimide is added portionwise over 5 minutes (to avoid foaming as the reaction warms to ca. 50° C.). After stirring 30 minutes 10 wt % of both triphenylphosphine (900 mg) and N-bromosuccinimide (600 mg) are added. After an additional 30 minutes stirring the reaction mixture is concentrated to approximately 10 ml, poured on a bed of Celite®, and then rinsed through with 0.1% methanol in dichloromethane. Evaporation of the filtrate provides 2.43 g of 5-chloro-2-nitrobenzyl bromide as a light yellow oil. ¹H-NMR (500 MHz, CDCl₃) δ (ppm) 4.806 (s, 2H), 7.457-7.479 (dd, 1H), 7.589-7.593 (s, 1H), 8.033-8.051 (d, 1H).

2.15 g of 5-chloro-2-nitrobenzylbromide is dissolved in approximately 25 ml methanol at room temperature. 1.86 g of 25% sodium methoxide in methanol is added and stirring continued for 0° C. 1 hour after which 10 wt % additional sodium methoxide is added to complete the conversion. The solvent is evaporated and the residue is dissolved in 100 ml dichloromethane and washed with 25 ml water (2×). Evaporation provided 1.6 g of 4-nitro-3-methoxymethylchlorobenzene. ¹H-NMR (500 MHz, CDCl₃) δ (ppm) 3.527 (s, 3H), 4.838 (s, 2H), 7.399-7.416 (dd, 1H), 7.824-7.826 (d, 1H), 8.066-8.084 (d, 1H).

The Ammonia Step—Preparation of 4-nitro-3-methoxymethylaminobenzene.

Embodiment A: Nucleophilic Displacement in Formamide

The reaction is performed in a 600 ml Parr stirred reactor with a sample dip tube (with stainless steel sintered frit on the tip), temperature control, pressure sensor, and a bottom drain port. The substrate (5 g of 4-nitro-3-methoxymethylchlorobenzene) is a solid that is suspended in formamide (225 g), heated to dissolve, and charged to the reactor under vacuum followed by a rinse to clear the lines. The reactor is purged of air by charging the reactor with nitrogen to greater than 70 psig (greater than 84.7 psi or greater than 584 kPa), vented, then vacuum is used to less than −13 psig (less than 1.7 psi or less than 11.7 kPa). These pressure/vent/vacuum cycles are performed three times. Ammonia (41 g) is added as a liquid under pressure from a charge tank placed on a balance. The reactor is charged with nitrogen to greater than 80 psig (greater than 94.7 psi or greater than 653 kPa). The reaction is heated to about 200° C. and stirred for about 6 hours, then cooled. Upon draining the material from the reactor, it is found that the reaction mixture is dark in color. The reaction mixture is evaporated to dryness on a rotary evaporator.

Figure 4:
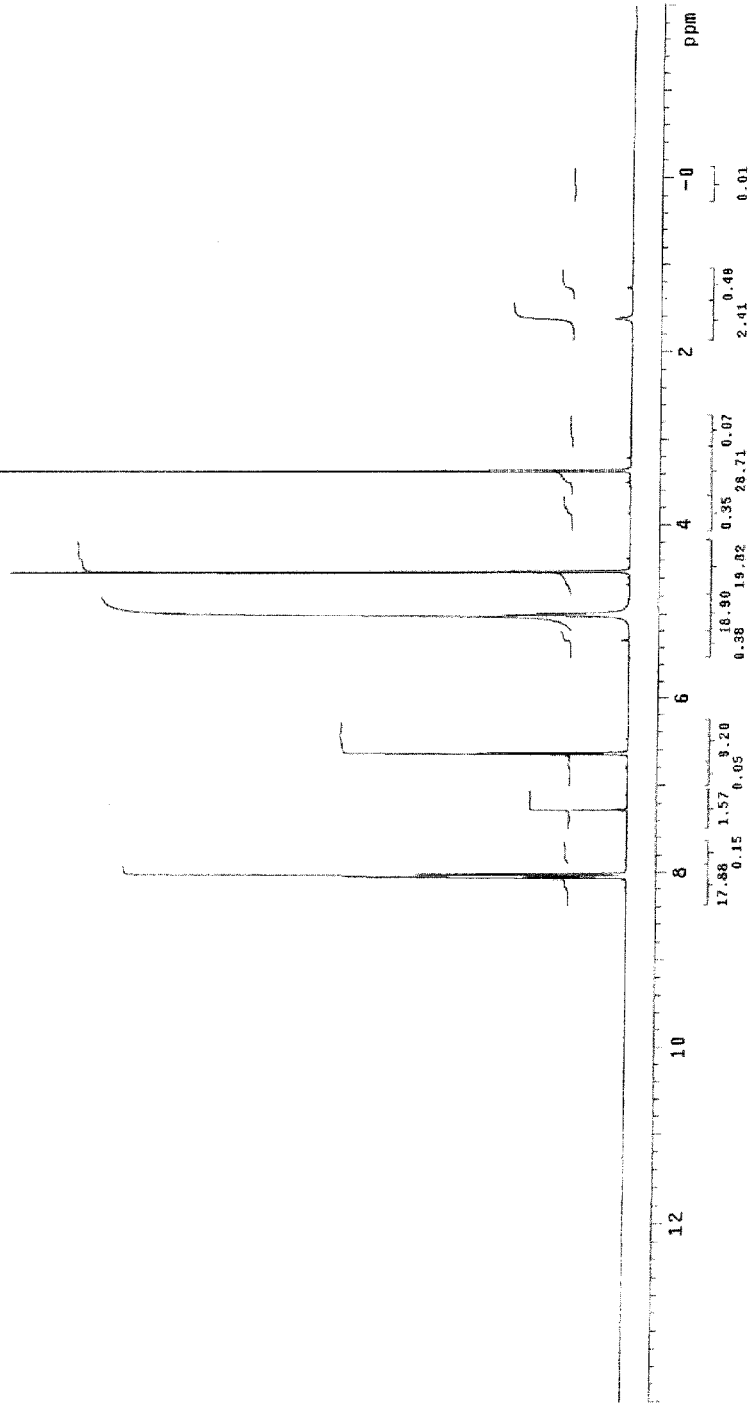
FIG. 4 shows an $^1$H NMR scan for formula (VIII) of the described method and process.

2.0 g Of the desired product is obtained in pure form. ISMS MH⁺ m/z 183. ¹H-NMR (CDCl₃, 500 MHz) δ 3.36 (s, 3H, CH₃), 4.526 (s, 2H, CH₂), 4.989 (s (br), 2H, NH2), 6.63-6.64 (d, J=8.79 Hz, 1H, arom.), 8.018-8.071 (m, 2H, arom.). See FIG. 4.

Embodiment B: Nucleophilic Displacement in Acetonitrile

The reaction is performed in a 600 ml Parr stirred reactor (about 250 rpm used throughout) with a sample dip tube (with stainless steel sintered frit on the tip), temperature control, pressure sensor, and a bottom drain port. The substrate (5 g) is a solid that is slurried in 10 ml of acetonitrile, heated to dissolve, and charged to the reactor under vacuum followed by a rinse to clear the lines. The reactor is purged of air by charging the reactor with nitrogen to greater than 70 psig (greater than 84.7 psi or greater than 584 kPa), vented, then vacuum is used to less than −13 psig (less than 1.7 psi or less than 11.7 kPa). These pressure/vent/vacuum cycles are performed three times. Ammonia (25 g) is added as a liquid under pressure from a charge tank placed on a balance. The reactor is charged with nitrogen to greater than 80 psig (greater than 94.7 psi or greater than 653 kPa). The reaction is heated to 210° C., kept there for approximately 24 hours, then cooled to room temperature. Upon draining the material from the reactor it is found that the reaction mixture is dark in color. The reaction mixture is evaporated to dryness on a rotary evaporator.

1.0 g Of the desired product is obtained in pure form. ISMS MH⁺ m/z 183. ¹H-NMR (CDCl₃, 500 MHz) δ 3.36 (s, 3H, CH₃), 4.526 (s, 2H, CH₂), 4.989 (s (br), 2H, NH2), 6.63-6.64 (d, J=8.79 Hz, 1H, arom.), 8.018-8.071 (m, 2H, arom.).

The Hydrogenation Step—Preparation of 2-methoxymethyl-1,4-benzenediamine 5 g (27.5 mmol) of 4-Nitro-2-methoxymethyl-aminobenzene and 0.250 g of palladium (10% on carbon) are placed in a 250 ml Parr bottle and 50 g of ethyl acetate is added. Hydrogenation is carried out using a Parr apparatus under 50-60 psig (64.7-74.7 psi or 446-515 kPa) of hydrogen pressure. In the course of the reaction the yellowish grey suspension turns to a darker grey suspension. The reaction is also carefully monitored for rapid hydrogen uptake and additional hydrogen is introduced to keep pressure above 50 psig (64.7 psi or 446 kPa). After 1 hour the suspension clears, leaving a yellow solution. The reaction is continued for 2.5 hours to ensure complete conversion. The catalyst is removed by filtration through glass microfiber filter paper. The filtrate is concentrated to ca. 25 ml, and 25 ml of toluene are added to precipitate the product. The product is collected on filter paper with suction and dried at 60° C. under vacuum. The product yield is 4.5 g.

Figure 5:
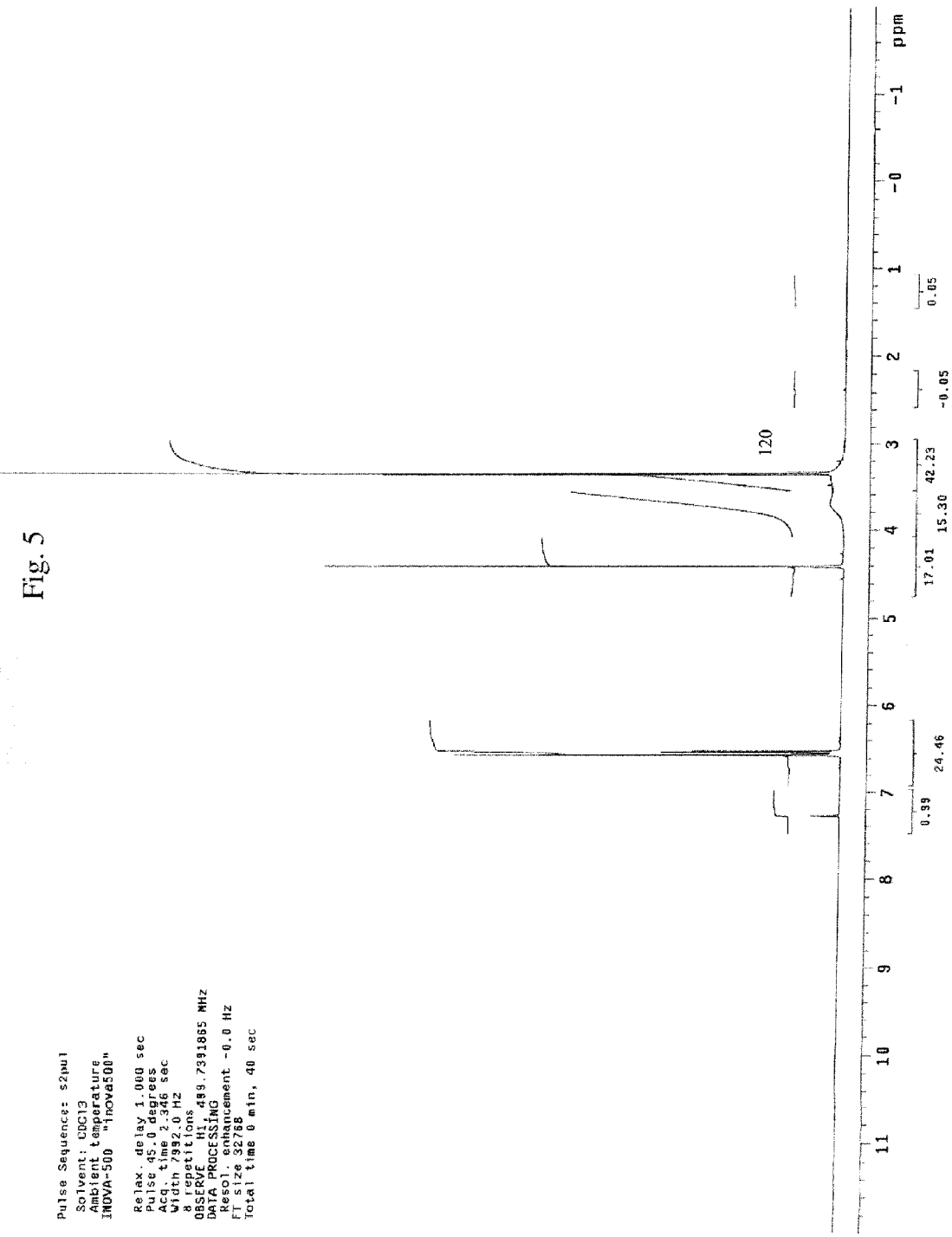
FIG. 5 shows an $^1$H NMR scan for 2-methoxymethyl-1,4-benzenediamine, formula (IV) of the described method and process.

¹H-NMR (DMSO-d₆): 6.41 (d), 1H, 6.37 (d), 1H, 6.33 (dd), 1H, 4.24 (s), 2H, 4.21 (s), 2H, 4.11 (s), 2H, 3.23 ppm (s), 3H See FIG. 5.

EXAMPLE 2

Preparation of
2-methoxymethyl-1,4-benzenediamine as an Adduct
with Malic Acid

The Acid Precipitating Step

Using the procedure described above, 80 g (0.44 mol) of 4-nitro-2-methoxymethylaminobenzene is hydrogenated in 240 ml of ethanol and 80 ml of water using 0.4 g of 10% Pd/C. The catalyst is removed by filtration and washed with 80 ml of ethanol under an inert atmosphere. The filtrate and wash solution are combined and added to a second solution of 66.7 g (0.483 mol) D,L-malic acid and 0.4 g sodium sulfite dissolved in a mixture of 320 ml ethanol and 40 ml water. The addition is carried out over a period of about 30 minutes. After the addition of about 50%, the final product starts to crystallize out. After the addition is completed, the obtained yellowish suspension is allowed to cool to room temperature with stirring over a period of about 30 minutes. The precipitate is filtered off and washed four times, with each wash using 60 ml of ethanol. The product is dried at 60° C. under vacuum. The product yield is 109 g.

Nuclear magnetic resonance (NMR) spectra are in accordance with the chemical structure and show the characteristic signal patterns of malic acid and 2-methoxymethyl-1,4-benzenediamine. See FIG. 6. Titration with perchloric acid and sodium hydroxide confirm the 1:1 stoichiometry of 2-methoxymethyl-1,4-benzenediamine with malic acid.

While the syntheses detailed herein have been described in embodiments of methods of making 2-methoxymethyl-1,4-benzenediamine and physiologically compatible salts thereof, such syntheses are not intended to be limited to the details shown, since various modifications and changes may be made without departing in any way from the spirit of the invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making 2-substituted-1,4-benzenediamine comprising:
    (a) introducing an ether forming agent to a 4-nitro-2- (or 3-) haloalkyl substituted chlorobenzene resulting in the 4-nitro-2 (or 3-) substituted-chlorobenzene:

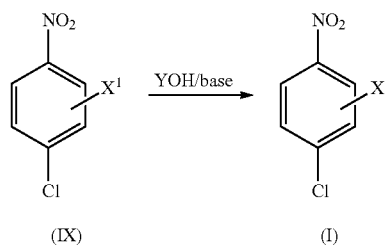

(b) introducing ammonia to a 4-nitro-2- (or 3-)substituted-chlorobenzene to obtain a 4-nitro-2- (or 3-)substituted-aminobenzene:

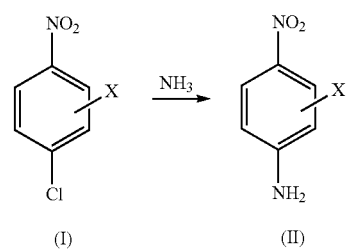

(c) hydrogenating the 4-nitro-2- (or 3-) substituted-aminobenzene in the presence of an hydrogenation catalyst to form a 2-substituted-1,4-benzenediamine:

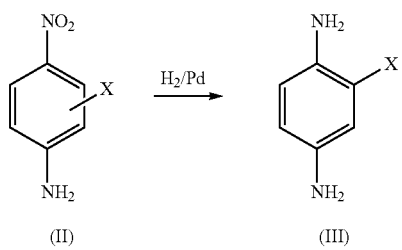

wherein $X^1$ of formula (IX) is selected from the group consisting of: a C1-C4 alkyl halogen,

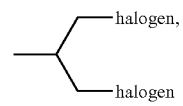

and mixtures thereof, wherein the halogen is F, Cl or Br;
wherein Y of YOH represents an alkyl moiety of C1-C3;
wherein the base is selected from suitable alkali alkoxides, alkali hydroxides, and mixtures thereof; and
wherein X of formulae (I)-(III)) is selected from the group consisting of:
    (a) methoxy, ethoxy, propoxy, isopropoxy, butoxy;
    (b) C1-C4 alkyl or branched alkyl with hydroxy substitution;
    (c) —(CH2)yOCH3, wherein y is from 1-3;
    (d) —(CH2)yOCH2CH3, wherein y is from 1-3;

(e) —(CH2)yOCH2CH2CH3, wherein y is from 1-3; and (f)

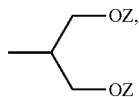

wherein Z is hydrogen, C1-3 alkyl, and mixtures thereof.

2. The method of claim 1 wherein the suitable alkali alkoxide is selected from the group consisting of sodium methoxide, lithium methoxide, potassium methoxide, sodium ethoxide, lithium ethoxide, potassium ethoxide, sodium propoxide, lithium propoxide, potassium propoxide and mixtures thereof.

3. The method of claim 1 wherein the suitable alkali hydroxide is sodium hydroxide or potassium hydroxide.

4. The method of claim 1 wherein the method further comprises dissolving a 4-nitro-2- (or 3-) haloalkyl moiety substituted chlorobenzene in an alcohol selected from methanol, ethanol and propanol to form a solution and then mixing the solution with an alkali alkoxide, alkali hydroxide and mixtures thereof.

5. The method of claim 4 wherein the suitable alkali alkoxide, alkali hydroxide and mixtures thereof is present in an amount from about 10% to about 30% by weight of the solution.

6. The method of claim 1 wherein the ether forming agent is introduced to a 4-nitro-2-haloalkyl substituted chlorobenzene to result in the 4-nitro-2-substituted-chlorobenzene:

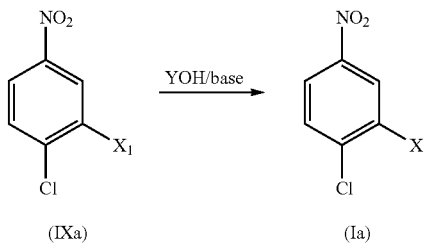

wherein X$^1$ of formula (IXa) is selected from a C1-C4 alkyl halogen,

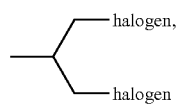

and mixtures thereof, wherein the halogen is F, Cl or Br; wherein X of formula (Ia) is selected from the group consisting of: (a) —(CH2)yOCH3; y is from 1-3 (b) —(CH2)yOCH2CH3; y is from 1-3 (c) —(CH2)yOCH2CH2CH3; y is from 1-3

(d)

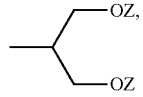

Z is hydrogen or C1-C3 alkyl; and mixtures thereof;
wherein Y of YOH represents an alkyl moiety of C1-C3; and
wherein the base is selected from the group consisting of alkali alkoxides, alkali hydroxides, and mixtures thereof.

7. The method of claim 1 wherein the ether forming agent is introduced to a 4-nitro-3-haloalkyl substituted chlorobenzene to result in the 4-nitro-3-substituted-chlorobenzene:

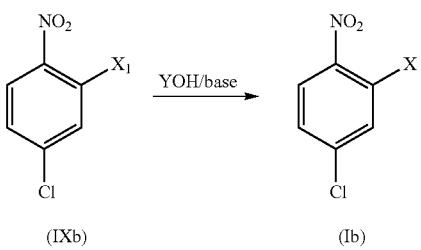

wherein X1 of formula (IXb) is selected from a C1-C4 alkyl halogen,

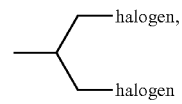

and mixtures thereof, wherein the halogen is F, Cl or Br; wherein X of formula (Ib) is selected from the group consisting of: (a) —(CH2)yOCH3; y is from 1-3 (b) —(CH2)yOCH2CH3; y is from 1-3 (c) —(CH2)yOCH2CH2CH3; y is from 1-3

(d)

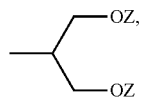

Z is hydrogen, C1-C3 alkyl, and mixtures thereof;
wherein Y of YOH represents an alkyl moiety of C1-C3; and wherein the base is selected from the group consisting of alkali alkoxides, alkali hydroxides, and mixtures thereof.

* * * * *